US009962134B2

(12) United States Patent
Brody

(10) Patent No.: US 9,962,134 B2
(45) Date of Patent: May 8, 2018

(54) APPARATUS AND METHOD FOR MAINTAINING IMAGE QUALITY WHILE MINIMIZING X-RAY DOSAGE OF A PATIENT

(71) Applicant: Medtronic Navigation, Inc., Louisville, CO (US)

(72) Inventor: Richard J. Brody, Clinton, MA (US)

(73) Assignee: Medtronic Navigation, Inc., Louisville, CO (US)

(*) Notice: Subject to any disclaimer, the term of this patent is extended or adjusted under 35 U.S.C. 154(b) by 373 days.

(21) Appl. No.: 14/925,440

(22) Filed: Oct. 28, 2015

(65) Prior Publication Data

US 2017/0119331 A1 May 4, 2017

(51) Int. Cl.
*G01N 23/04* (2006.01)
*A61B 6/00* (2006.01)

(52) U.S. Cl.
CPC .............. *A61B 6/488* (2013.01); *A61B 6/469* (2013.01); *A61B 6/5294* (2013.01); *A61B 6/544* (2013.01); *A61B 6/545* (2013.01)

(58) Field of Classification Search
CPC ....... A61B 6/469; A61B 6/488; A61B 6/5294; A61B 6/544; A61B 6/545; A61B 6/541; A61B 6/12; A61B 6/5217; A61B 34/20; A61B 5/7285; A61B 6/5247; A61B 8/543; A61B 6/504; A61B 6/481; A61B 6/503; A61B 17/12036; A61B 17/1204; A61B 17/12136; A61B 18/02; A61B 18/1492; A61B 18/24
(Continued)

(56) References Cited

U.S. PATENT DOCUMENTS 7,480,365 B1 * 1/2009 Topfer .................. A61B 6/032 378/108
7,620,142 B1 11/2009 Toth
(Continued)

FOREIGN PATENT DOCUMENTS

JP 2010264163 A 11/2010
WO WO-2013/042514 A1 3/2013

OTHER PUBLICATIONS

International Search Report and Written Opinion, dated Jan. 23, 2017 in PCT/US2016/057945.

*Primary Examiner* — Irakli Kiknadze
(74) *Attorney, Agent, or Firm* — Harness Dickey

(57) ABSTRACT

A system including initialization, imaging, alignment, processing, and setting modules. The initialization module obtains patient parameters for a patient and procedure and surgeon parameters. The initialization module selects first settings for an x-ray source based on the patient, procedure, and surgeon parameters. The image module obtains a first sample set of images of a region-of-interest of the patient and a master sample set of images. The first sample set was acquired as a result of the x-ray source operating according to the first settings. The alignment module aligns the first sample set to the master sample set. The processing module processes pixel data corresponding to a result of the alignment based on a pixel parameter or one of the patient parameters. The setting module adjusts the first settings to provide updated settings. X-ray dosage associated with the updated settings is less than x-ray dosage associated with the first settings.

36 Claims, 6 Drawing Sheets

(58) Field of Classification Search
USPC .......................................... 378/4, 16, 19, 62
See application file for complete search history.

(56) References Cited

U.S. PATENT DOCUMENTS

| | | | |
|---|---|---|---|
| 7,853,476 | B2 | 12/2010 | Reiner |
| 8,018,487 | B2 | 9/2011 | Reiner |
| 8,175,894 | B2 | 5/2012 | Oowaki et al. |
| 8,412,544 | B2 | 4/2013 | Reiner |
| 8,445,878 | B2 | 5/2013 | Guez |
| 8,538,776 | B2 | 9/2013 | Reiner |
| 2004/0101105 | A1 | 5/2004 | Segawa et al. |
| 2007/0071172 | A1 | 3/2007 | Mollus et al. |
| 2008/0103834 | A1 | 5/2008 | Reiner |
| 2008/0165927 | A1 | 7/2008 | Wedel |
| 2009/0006131 | A1 | 1/2009 | Unger et al. |
| 2010/0091950 | A1* | 4/2010 | Ellinwood .............. H05G 1/30 378/97 |
| 2011/0257919 | A1 | 10/2011 | Reiner |
| 2014/0341350 | A1 | 11/2014 | Muroi et al. |

* cited by examiner

IPM
NCM
SCM
GCM
NCM
SCM

APPARATUS AND METHOD FOR MAINTAINING IMAGE QUALITY WHILE MINIMIZING X-RAY DOSAGE OF A PATIENT

FIELD

The present disclosure relates to x-ray imaging systems, and more particularly to control systems for controlling x-ray dosage of an x-ray scanner.

BACKGROUND

This section provides background information related to the present disclosure which is not necessarily prior art.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the patient based on images of the patient, which can be acquired using an x-ray scanner having an imaging system. The images may be acquired prior to, during and/or subsequent to the procedure. The imaging system may be, for example, an O-Arm® medical imaging system such as those sold by Medtronic, Inc. or C-Arm imaging system. The images may be fluoroscopic or radiographic images depending on an operating mode of the imaging system.

The acquired images of the patient can assist a surgeon in planning and performing the procedure, as well as evaluating results of the procedure. A surgeon may select a two dimensional image or a three dimensional image representation of the patient. The images can assist the surgeon in performing a procedure with a less invasive technique by allowing the surgeon to view the anatomy of the patient without removing overlying tissue (including dermal and muscular tissue) when performing a procedure.

An O-Arm imaging system includes an 'O'-shaped gantry and an 'O'-shaped rotor. A C-Arm imaging system includes a 'C'-shaped gantry and a 'C'-shaped rotor. Each of these imaging systems typically includes an x-ray source and an x-ray detector mounted opposite each other on the corresponding rotor. Each of the x-ray sources generates x-rays, which are directed at a subject. Each of the x-ray detectors detects the x-rays subsequent to the x-rays passing through the subject.

As an example, an imaging system may include an x-ray source, an x-ray detector, and a generator. The generator converts a low-voltage (e.g., 400 volts (V)) to a high-voltage (e.g., 150 kilo-volts (kV)). The high-voltage is provided to the x-ray source to generate x-rays. For a same dosage period and amount of current, the higher the low-voltage and thus the higher the high-voltage, the higher the dosage of x-rays received by the patient. Similarly, for the same low-voltage, the higher the current level and/or the longer the dosage period, the higher the dosage of x-rays received by the patient.

The voltage, current and dosage periods can be adjusted by a surgeon (or system operator). A surgeon may intuitively increase the voltage, current and/or dosage periods in an attempt to provide improved images. This not only increases x-ray dosage to a patient, but can also decrease quality of acquired images. Increasing voltage, current and/or dosage periods can cause: x-ray detectors to be overloaded; images to be "grainy" and/or "spotted"; and/or image quality to decrease during a procedure.

SUMMARY

This section provides a general summary of the disclosure, and is not a comprehensive disclosure of its full scope or all of its features. According to various embodiments, provided is a system that includes an initialization module, an imaging module, an alignment module, a processing module, and setting module. The initialization module is configured to obtain patient parameters for a patient, procedure parameters, and surgeon parameters. The initialization module is configured to select first settings for an x-ray source based on the patient parameters, the procedure parameters, and the surgeon parameters. The image module is configured to obtain (i) a first sample set of one or more images of a region-of-interest of the first patient, and (ii) a master sample set of one or more images. The first sample set of one or more images were acquired as a result of the x-ray source operating according to the first settings. The alignment module is configured to align the first sample set of one or more images to the master sample set of one or more images. The processing module is configured to process pixel data corresponding to a result of the alignment based on a pixel parameter or one of the patient parameters. The setting module is configured to adjust the first settings to provide updated settings. X-ray dosage associated with the updated settings is less than x-ray dosage associated with the first settings.

In other features, a method is provided and includes obtaining patient parameters for a first patient, procedure parameters, and surgeon parameters, where the initialization module is configured to select first settings for an x-ray source based on the patient parameters, the procedure parameters, and the surgeon parameters. The method further includes obtaining (i) a first sample set of one or more images of a region-of-interest of the first patient, and (ii) a master sample set of one or more images, where the first sample set of one or more images were acquired as a result of the x-ray source operating according to the first plurality of settings. The method yet further includes: aligning the first sample set of one or more images to the master sample set of one or more images; processing pixel data corresponding to a result of the alignment based on a pixel parameter or one of the patient parameters; and adjusting the first settings to provide updated settings, where x-ray dosage associated with the updated settings is less than x-ray dosage associated with the first plurality of settings.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
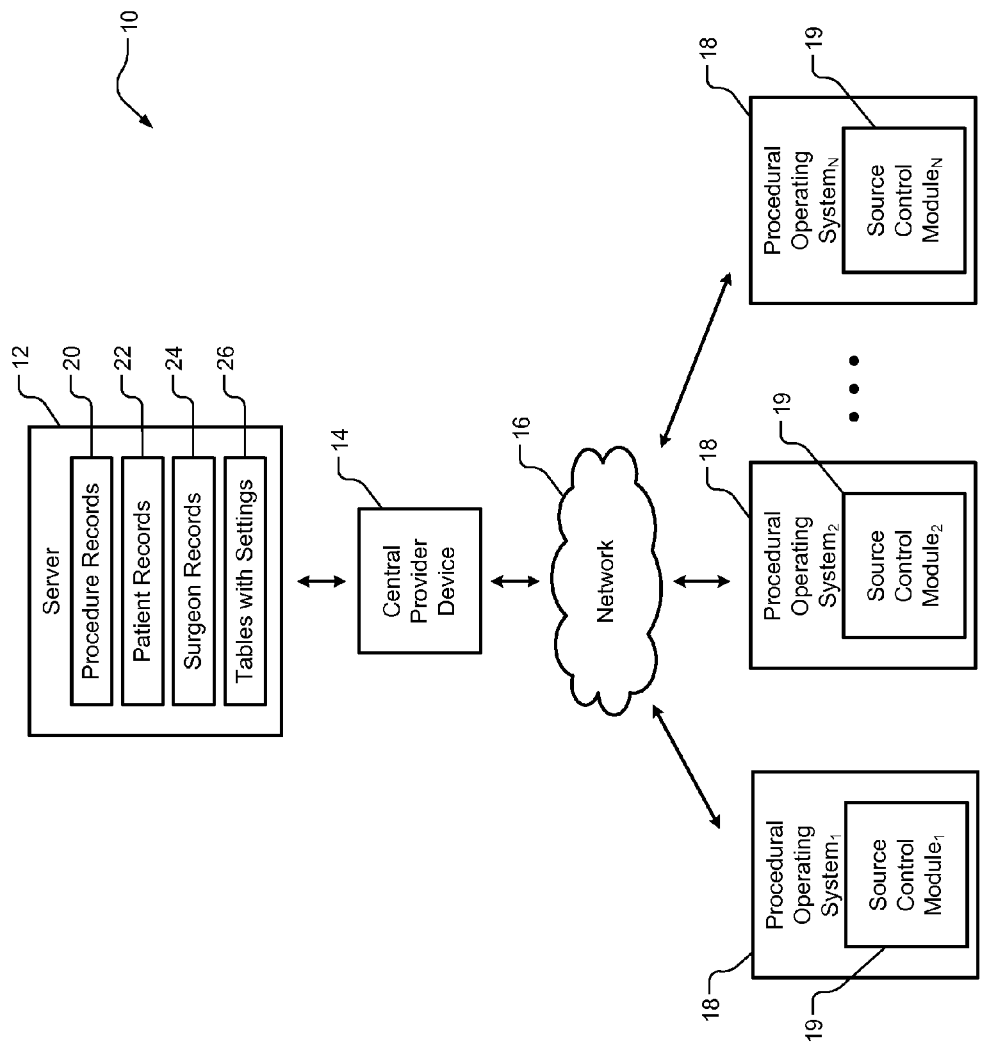
FIG. 1 is a functional block diagram of an imaging network including procedural operating systems with source control modules in accordance with an embodiment of the present disclosure.

Imaging systems and methods are disclosed herein that maintain or improve image quality and minimize x-ray dosages of patients over traditional imaging systems. The disclosed imaging systems can be considered intelligent imaging systems that monitor, track and learn imaging system and surgeon parameters associated with x-ray dosages generated during various procedures. The imaging systems monitor trends and provide feedback to the surgeons to improve settings for improved image quality and reduced x-ray dosage.

The following description is merely exemplary in nature. It should be understood that throughout the drawings, corresponding reference numerals indicate like or corresponding parts and features. Although the following teachings are primarily described with respect to an imaging system, such as an O-Arm® medical imaging system such as those sold by Medtronic, Inc. or C-Arm imaging system, the teachings may be applied to other imaging systems.

Figure 2:
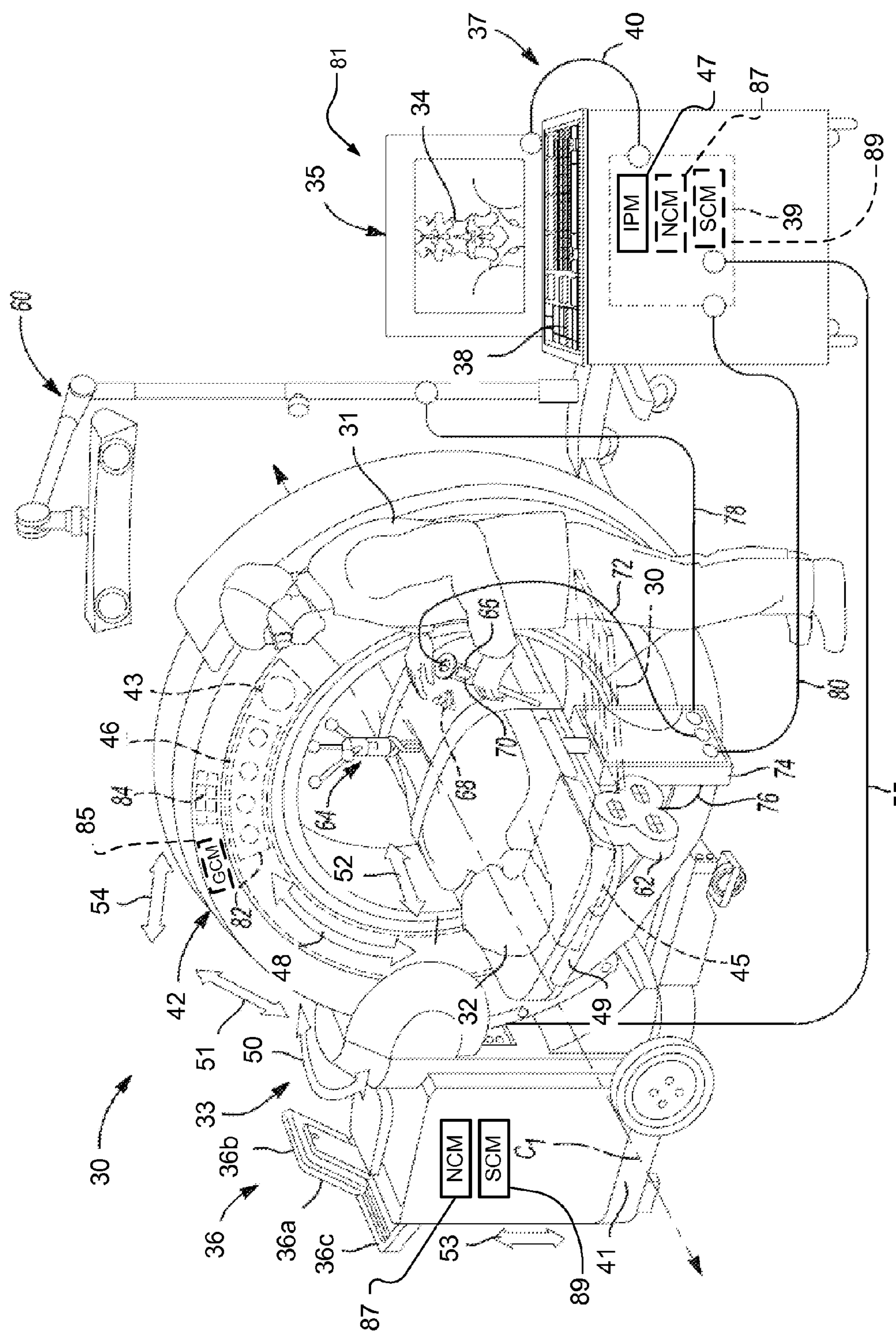
FIG. 2 is an environmental view of an imaging system including a source control module in accordance with an embodiment of the present disclosure.

FIG. 1 shows an imaging network 10 that may include a server 12, a central provider device 14, a network 16, and procedural operating systems 18. A procedural operating system may be located at a site and include a navigation system and an imaging system, as further described below. Each of the procedural operating systems 18 includes a source control module 19. The source control modules 19 control x-rays sources (an example of which is shown in FIG. 2) for x-ray imaging performed by the procedural operating systems 18. Various parameters are monitored, tracked and stored in the procedural operating systems 18, which may be transmitted to the central provider device 14 via the network 16. The source control modules 19 may generate recommended settings for x-ray imaging and/or receive recommended settings from the central provider device 14. The central provider device 14 may generate recommended settings based on the parameters received from the procedural operating systems 18. The server 12, central provider device 14 and procedural operating systems 18 may include respective memories and transceivers for storing and transmitting the parameters. The network 16 may be a local area network, a wide area network, a wireless network, etc. The network 16 may include an Internet.

The server 12 may store records, such as procedure records 20, patient records 22, and surgeon records 24, as well as tables 26. The procedure records 20 may store procedure parameters corresponding to respective procedures. The procedure parameters may include recommended parameters and/or provider parameters. The recommended parameters may be parameters recommended based on monitored, tracked, and/or historical values, predetermined values, and/or provider parameters. The provider parameters may be parameters recommended by a provider (e.g., the central provider device 14). The recommended parameters and the provider parameters may each include imaging system settings used during different procedures and conducted by different surgeons. The imaging system settings may include x-ray source voltages (e.g., in kilo-volts), generator voltages, current levels (e.g., in milli-amperes), dosage periods (e.g., in seconds), and/or other imaging system settings. The recommended parameters and the provider parameters may be determined by the source control modules 19 and/or the central provider device 14. The central provider device 14 may generate the recommended parameters and/or the provider parameters based on the parameters collected and/or recommended by the source control modules 19.

The patient records 22 may each include patient parameters. Each of the patient records may include parameters for a particular patient and corresponding procedure. More than one record may be stored for a patient that has or is to undergo multiple procedures. The patient parameters for each record may include: a patient identifier (ID); weight of the patient; one or more regions-of-interest (ROIs); size of the patient (e.g., dimensions of patient); volume of a portion of or a whole body of the patient; shape of an organ, a bone, a ROI, or other portion of the patient; gender; age; medical history; ID of anatomy (e.g., ID of cranium, knee, spine, or other portion of the patient); ID of ROI; and/or other patient parameters. The size and/or weight of the patient can be indicative of a percentage of fat tissue in the patient. A ROI may include one or more body parts. The dimensions of the patient may include dimensions of body parts and/or a whole body of the patient. The dimensions may be simple to include, for example, height, width, length or may be complex dimensions to identify a periphery (or outer dimensions) of the body part or whole body. The dimensions may be of internal organs or bones. The dimensions may be of ROIs.

The surgeon records may include parameters for respective surgeons and corresponding procedures. Each record may be associated with a particular surgeon, a particular procedure, and/or one or more patients having similar patient parameters. Each record may include surgeon parameters, which may include: an ID of the surgeon; low and/or high x-ray source voltages for each patient; generator voltages; generator current levels; x-ray source current levels for each patient; typical surgeon low and/or high x-ray source voltages for the particular procedure; typical surgeon x-ray source current levels for the particular procedure; last used low and/or high x-ray source voltages; last used x-ray source current levels; dosage periods for a particular patient; typical and/or last used dosage periods; x-ray source duty cycles; x-ray source ON periods; x-ray source OFF periods; etc.

The tables 26 may relate the parameters and/or settings stored in the records 20, 22, 24 to recommended x-ray source settings. The tables 26 are not static, but rather may be continuously modified and added to prior to, during and/or subsequent to procedures performed. The recommended x-ray source settings may be based on determined image quality values and x-ray dosages. The recommended x-ray source settings may be predetermined, determined by one or more of the source control modules 19, and/or determined by the central provider device 14, as described above. The recommended x-ray source settings may be based on image quality values determined by an image control module (an example of which is shown in FIG. 2) and/or the source control modules 19 and/or indicated by surgeons during and/or subsequent to corresponding performed procedures. The indicated image quality values may be input by the surgeons to the source control modules 19. A procedure may be done on a cadaver or a live patient.

FIG. 2 shows an operating theatre (or inside of an operating room) 30 and a user 31 (e.g., a physician) performing a procedure on a subject (e.g., a patient) 32. In performing the procedure, the user 31 uses an imaging system 33 to acquire image data of the patient 32. The image data acquired of the patient 32 can include two-dimensional (2D) or three-dimensional (3D) images. Models may be generated using the acquired image data. The model can be a three-dimension (3D) volumetric model generated based on the acquired image data using various techniques, including algebraic iterative techniques. The image data (designated 34) can be displayed on a display device 35, and additionally, may be displayed on a display device 36*a* associated with an imaging computing system 36. The displayed image data 34 may include 2D images, 3D images, and/or a time changing 4D images. The displayed image data 34 may also include acquired image data, generated image data, and/or a combination of the acquired and generated image data.

Image data acquired of the patient 32 may be acquired as 2D projections. The 2D projections may then be used to reconstruct 3D volumetric image data of the patient 32. Also, theoretical or forward 2D projections may be generated from the 3D volumetric image data. Accordingly, image data may be used to provide 2D projections and/or 3D volumetric models.

The display device 35 may be part of a computing system 37. The computing system 37 may include a variety of computer-readable media. The computer-readable media may be any available media that is accessed by the computing system 37 and may include both volatile and non-volatile media, and removable and non-removable media. By way of example, the computer-readable media may include computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 37. The computer-readable media may be accessed directly or through a network such as the Internet.

In one example, the computing system 37 can include an input device 38, such as a keyboard, and one or more processors 39 (the one or more processors may include multiple-processing core processors, microprocessors, etc.) that may be incorporated with the computing system 37. The input device 38 may include any suitable device to enable a user to interface with the computing system 37, such as a touchpad, touch pen, touch screen, keyboard, mouse, joystick, trackball, wireless mouse, audible control or a combination thereof. Furthermore, while the computing system 37 is described and illustrated herein as comprising the input device 38 discrete from the display device 35, the computing system 37 may include a touchpad or tablet computing device and may be integrated within or be part of the computing system 37. A connection (or communication line) 40 may be provided between the computing system 37 and the display device 35 for data communication to allow driving the display device 35 to illustrate the image data 34.

The imaging system 33 may be an O-Arm imaging system, a C-Arm imaging system or other suitable imaging system. The imaging system 33 may include a mobile cart 41, the imaging computing system 36 and a gantry 42 (or x-ray scanner gantry). The gantry 42 includes an x-ray source 43, a collimator (not shown), a multi-row detector 44, a flat panel detector 45 and a rotor 46. The x-ray source 43 may include a generator and/or may be connected to a generator. With reference to FIG. 2, the mobile cart 41 may be moved from one operating theater or room to another and the gantry 42 may be moved relative to the mobile cart 41. This allows the imaging system 33 to be mobile and used for various procedures without requiring a capital expenditure or space dedicated to a fixed imaging system. Although the gantry 42 is shown as being mobile, the gantry 42 may not be connected to the mobile cart 41 and may be in a fixed position.

The gantry 42 may define an isocenter of the imaging system 33. In this regard, a centerline C1 through the gantry 42 defines an isocenter or center of the imaging system 33. Generally, the patient 32 can be positioned along the centerline C1 of the gantry 42, such that a longitudinal axis of the patient 32 is aligned with the isocenter of the imaging system 33.

The imaging computing system 36 may control the movement, positioning and adjustment of the multi-row detector 44, the flat panel detector 45 and the rotor 46 independently to enable image data acquisition via an image processing module 47 of the processor 39. The processed images may be displayed on the display device 35.

During operation, the x-ray source 43 emits x-rays through the patient 32, which are detected by the multi-row detector 44 or the flat panel detector 45. The x-rays emitted by the x-ray source 43 may be shaped by the collimator and emitted for detection by the multi-row detector 44 or the flat panel detector 45. The collimator may include one or more leaves, which may be controlled to shape the x-rays emitted by the x-ray source 43. The collimator may shape the x-rays emitted by the x-ray source 43 into a beam that corresponds with the shape of the multi-row detector 44 and the flat panel detector 45. The multi-row detector 44 may be selected to acquire image data of low contrast regions of the anatomy, such as regions of soft tissue. The flat panel detector 45 may be selected to acquire image data of high contrast regions of the anatomy, such as bone. The x-ray source 43, the collimator, the multi-row detector 44 and the flat panel detector 45 may each be coupled to and/or mounted on the rotor 46.

The multi-row detector 44 and the flat panel detector 45 may be coupled to the rotor 46 to be (i) diametrically opposed from the x-ray source 43 and the collimator within the gantry 42, and (ii) independently movable relative to each other and into alignment with the x-ray source 43 and the collimator. In one example, the multi-row detector 44 may be positioned such that the flat panel detector 45 may be adjacent to the multi-row detector 44. In one alternative example, the flat panel detector 45 may be moved over the multi-row detector 44 into alignment with the x-ray source 43 when an image using the flat panel detector 45 is acquired. In another example, the multi-row detector 44 may be positioned over the flat panel detector 45. As a further alternative, the multi-row detector 44 and the flat panel detector 45 may each be separately movable, such that the selected multi-row detector 44 or flat panel detector 45 may be aligned with the x-ray source 43 and the collimator. The selected one of the multi-row detector 44 and the flat panel detector 45 may be aligned with the x-ray source 43 and the collimator when the selected one of the multi-row detector 44 and the flat panel detector 45 is substantially opposite or about 180 degrees apart from the x-ray source 43 and the collimator.

As the x-ray source 43, collimator, multi-row detector 44 and flat panel detector 45 are coupled to the rotor 46, the x-ray source 43, collimator, multi-row detector 44 and flat panel detector 45 are movable within the gantry 42 about the patient 32. Thus, the multi-row detector 44 and the flat panel detector 45 are able to be rotated in a 360° motion around the patient 32, as indicated by arrow 48. The x-ray source 43 and collimator may move in concert with at least one of the multi-row detector 44 and the flat panel detector 45 such that the x-ray source 43 and collimator remain generally 180° apart from and opposed to the multi-row detector 44 or flat panel detector 45.

The gantry 42 has multiple degrees of freedom of motion. The gantry 42 may be isometrically swayed or swung (herein also referred to as iso-sway) relative to table 49 on which the patient 32 is disposed. The isometric swing is indicated by arrow 50. The gantry 42 may be: tilted relative to the patient 32 (as indicated by arrow 51); moved longitudinally relative to the patient 32 (as indicated by arrow 52); moved up and down relative to the mobile cart 41 and transversely to the patient 32 (as indicated by arrow 53); and moved away from or towards the mobile cart 41 (as indicated by arrow 54). These different degrees of freedom of motion of the gantry 42 allow the x-ray source 43, collimator, multi-row detector 44 and flat panel detector 45 to be positioned relative to the patient 32.

The imaging system 33 may be precisely controlled by the imaging computing system 36 to move the x-ray source 43, collimator, the multi-row detector 44 and the flat panel detector 45 relative to the patient 32 to generate precise image data of the patient 32. In addition, the imaging system 33 may be connected with the processor 39 via connection 55 which includes a wired or wireless connection or physical media transfer from the imaging system 33 to the processor 39. Thus, image data collected with the imaging system 33 may also be transferred from the imaging computing system 36 to the computing system 37 for navigation, display, reconstruction, etc.

The imaging system 33 may also be used during an unnavigated or navigated procedure. In a navigated procedure, a localizer, including either or both of an optical localizer 60 and an electromagnetic localizer 62, may be used to generate a field or receive or send a signal within a navigation domain relative to the patient 32. If desired, the components associated with performing a navigated procedure may be integrated within the imaging system 33. The navigated space or navigational domain relative to the patient 32 may be registered to the image data 34 to allow registration of a navigation space defined within the navigational domain and an image space defined by the image data 34. A patient tracker (or a dynamic reference frame) 64 may be connected to the patient 32 to allow for a dynamic registration and maintenance of the registration of the patient 32 to the image data 34.

An instrument 66 may then be tracked relative to the patient 32 to allow for a navigated procedure via a navigation system 81. The instrument 66 may include an optical tracking device 68 and/or an electromagnetic tracking device 70 to allow for tracking of the instrument 66 with either or both of the optical localizer 60 or the electromagnetic localizer 62. The instrument 66 may include a communication line 72 with a navigation interface device 74, which may communicate with the electromagnetic localizer 62 and/or the optical localizer 60. The navigation interface device 74 may then communicate with the processor 47 via a communication line 80. The connections or communication lines 40, 55, 76, 78, or 80 can be wire based as shown or the corresponding devices may communicate wirelessly with each other.

The instrument 66 may be an interventional instrument and/or an implant. Implants may include a ventricular or vascular stent, a spinal implant, neurological stent or the like. The instrument 66 may be an interventional instrument such as a deep brain or neurological stimulator, an ablation device, or other appropriate instrument. Tracking the instrument 66 allows for viewing the location of the instrument 66 relative to the patient 32 with use of the registered image data 34 and without direct viewing of the instrument 66 within the patient 32. For example, the instrument 66 may be graphically illustrated as an icon superimposed on the image data 34.

Further, the imaging system 33 may include a tracking device, such as an optical tracking device 82 or an electromagnetic tracking device 84 to be tracked with a respective optical localizer 60 or the electromagnetic localizer 62. The tracking devices 82, 84 may be associated directly with the x-ray source 43, multi-row detector 44, flat panel detector 45, rotor 46, the gantry 42, or other appropriate part of the imaging system 33 to determine the location or position of the x-ray source 43, multi-row detector 44, flat panel detector 45, rotor 46 and/or gantry 42 relative to a selected reference frame. As illustrated, the tracking devices 82, 84 may be positioned on the exterior of the housing of the gantry 42. Accordingly, portions of the imaging system 33 including the instrument 66 may be tracked relative to the patient 32 to allow for initial registration, automatic registration or continued registration of the patient 32 relative to the image data 34.

The image processing module (IPM) 47 may receive user input data from the input device 36*c* and may output the image data 34 to the display device 35 or the display device 36*a*. The user input data may include a request to acquire image data of the patient 32. Based on the user input data, the IPM 47 may generate a detector signal and a motion signal. The detector signal may include a selected detector for image acquisition. The motion signal may include a motion profile for the rotor 46 to move to a selected location to acquire image data. The motion signal may be a command or instruction signal that is provided from the IPM 47 to a gantry control module 85. The gantry control module 85 may be included in the gantry 42 and on the rotor 46 and position the rotor 46 based on the instruction signal.

The processor 39 or the mobile cart 41 may include a navigation control module (NCM) 87 and source control module (SCM) 89 (e.g., one of the SCMs 19 of FIG. 1). The NCM 87 tracks the instrument 66 relative to the patient 32 to allow for illustration of the tracked location of the instrument 66 relative to the image data 34 for performing a procedure. The SCM 89 may control, monitor, track, adjust and/or set x-ray source parameters (e.g., x-ray source voltages, current levels and/or dosage periods). The SCM 89 may access procedure, patient, surgeon and/or recommended parameters based on previous used, current and/or inputted x-ray source parameters. The SCM 89 may provide recommended x-ray source parameters based on the accessed procedure, patient, surgeon and/or recommended parameters and/or the previously used, current and/or inputted x-ray source parameters. This is described in further detail below. The IPM 47, NCM 87 and SCM 89 may communicate with each other and share data. The IMP 47, NCM 87 and SCM 89 may be implemented as separate modules as shown or may be implemented as a single module.

The IMP 47, NCM 87 and SCM 89 may be implemented in the imaging computing system 36, on the mobile cart 30, or as part of the processor 26. The IPM 47 and/or SCM 89 may send a source signal to the x-ray source 43. The source signal may command the x-ray source 43 to output or emit at least one or more x-ray pulses. The x-ray pulses are generated based on x-ray source parameters set by the SCM 89. The IPM 47 and/or SCM 89 may send a collimator signal to the collimator. The collimator signal may indicate a selected shape of one or more collimated x-ray pulses. The selected shape of the collimated x-ray pulses may correspond to the selected one of the multi-row detector 44 and the flat panel detector 45. In this regard, if the multi-row detector 44 is selected, the collimated x-ray pulses may be shaped by the collimator to match the shape of the multi-row detector 44. If the flat panel detector 45 is selected, then the collimated x-ray pulses may be shaped by the collimator to match the shape of the flat panel detector 45.

The IPM 47 may also receive as input a multi-row detector signal, which may include the one or more collimated x-ray pulses detected by the multi-row detector 44. The image processing module 47 may receive as input a flat panel detector signal, which may include the one or more collimated x-ray pulses detected by the flat panel detector 45. Based on the received collimated x-ray pulses, the image processing module 47 may generate the image data 34.

In one example, the image data 34 may include a single 2D image. In another example, the image processing module 47 may perform automatic reconstruction of an initial 3D model of an area of interest of the patient 32. Reconstruction of the 3D model may be performed in any appropriate manner, such as using algebraic techniques for optimization. The algebraic techniques may include Expectation maximization (EM), Ordered Subsets EM (OS-EM), Simultaneous Algebraic Reconstruction Technique (SART) and total variation minimization. A 3D volumetric reconstruction may be provided based on the 2D projections.

The algebraic techniques may include an iterative process to perform a reconstruction of the patient 32 for display as the image data 34. For example, a pure or theoretical image data projection, based on or generated from an atlas or stylized model of a "theoretical" patient, may be iteratively changed until the theoretical projection images match the acquired 2D projection image data of the patient 32. Then, the stylized model may be appropriately altered as the 3D volumetric reconstruction model of the acquired 2D projection image data of the patient 32 and may be used in a surgical intervention, such as navigation, diagnosis, or planning interventions. In this regard, the stylized model may provide additional detail regarding the anatomy of the patient 32, which may enable the user 31 to plan the surgical intervention efficiently. The theoretical model may be associated with theoretical image data to construct the theoretical model. In this way, the model or the image data 34 may be built based upon image data acquired of the patient 32 with the imaging system 33. The IPM 47 may output the image data 34 to the display device 36*a*.

The processor 39 may receive as an input the detector signal and the motion signal from the IPM 47. The processor 39, based on the detector signal and/or the motion signal may transmit (via wires or wirelessly) control signals to the GCM 85. The GCM 85 may be located on the rotor 46. Based on the detector signal, the GCM 85 may generate a first move signal to move the selected one of the multi-row detector 44 or the flat panel detector 45 into alignment with the x-ray source 43 and the collimator. Based on the motion signal, the GCM 85 may also generate a second move signal for the rotor 46 to move or rotate the rotor 46 within the gantry 42 relative to the patient 32. The movement of the x-ray source 43, the collimator, the multi-row detector 44 and the flat panel detector 45 about the patient 32 may be controlled to acquire image data at selected locations and orientations relative to the patient 32.

The 2D image data may be acquired at each of multiple annular positions of the rotor 46. The 3D image data may be generated based on the 2D image data. Also, the gantry 42, the x-ray source 43, the multi-row detector 44 and the flat panel detector 45 may not be moved in a circle, but rather may be moved in another pattern, such as a spiral helix, or other rotary movement about or relative to the patient 32. This can reduce exposure of a patient to radiation. The pattern (or path) may be non-symmetrical and/or non-linear based on movements of the imaging system 33, such as the gantry 42. In other words, the path may not be continuous in that the gantry 42 may be stopped and moved back in a direction along the path the gantry 42 previously followed. This may include following previous oscillations of the gantry 42.

Inputs to the imaging system 33 may be received at the input device 36*c*, input device 38, or other control modules (not shown) within the computing system 37 or imaging computing system 36, and/or determined by other submodules (not shown) within the IPM 47. The IPM 47 may receive user input data requesting that image data of the patient 32 be acquired. The input data may include information as to whether the region-of-interest on the patient 32 is a high contrast region (e.g. boney tissue) or a low contrast region (e.g. soft tissue). In one example, the user input data may include a region-of-interest on the anatomy of the patient 32. The IPM 47 may automatically determine to use the multi-row detector 44 or the flat panel detector 45 based on the region-of-interest. For example, the user may select (i) the multi-row detector 44 to acquire an image of soft tissue, and (ii) the flat panel detector 45 to acquire an image of boney tissue.

Based on the user input data, the IPM 47 and/or the SCM 89 may generate source data and detector type data. The IPM 47 may also generate motion profile data and collimator data. The source data may include information to output x-ray pulses or a signal to power-down the imaging system 33. The detector type data may include the selected multi-row detector 44 or flat panel detector 45 to acquire the image data. The motion profile data may include a selected profile for the movement of the rotor 46 within the gantry 42. The collimator data may include information to shape the x-ray pulses into collimated x-ray pulses to match the selected one of the multi-row detector 44 and flat panel detector 45.

The IPM 47 may also receive as an input multi-row detector data and flat panel detector data. The multi-row detector data may indicate the energy from the collimated x-ray pulses received by the multi-row detector 44. The flat panel detector data may indicate the energy from the collimated x-ray pulses received by the flat panel detector 45. Based on the multi-row detector data and the flat panel detector data, the IPM 47 may generate the image data 34 and may output this image data 34 to the display device 36*a* or display device 35.

The processor 39 may receive as input the detector type data and the motion profile data. Based on the detector type data, the processor 39 may generate flat panel move data or multi-row move data (and/or corresponding signals). The flat panel move data may include a selected position for the flat panel detector 45 to move to in order to be aligned with the x-ray source 43 and collimator. The multi-row move data may include a selected position for the multi-row detector 44 to move in order to be aligned with the x-ray source 43 and collimator.

The processor 39 or a module thereof, based on the source data, may cause the x-ray source 43 to generate pulse data for control of the collimator. The pulse data may include pulse data for at least one x-ray pulse. The processor 39 and/or a module thereof may receive as an input the multi-row move data and the collimated pulse data. Based on the multi-row move data, the multi-row detector 44 may move into alignment with the x-ray source 43. Based on the received pulse data, the processor 39 and/or a module thereof may generate the multi-row detector data (and/or a corresponding signal) for the IPM 47. The processor 39 and/or a module thereof may receive as an input the flat panel move data and the collimated pulse data. Based on the flat panel move data, the flat panel detector 45 may move into alignment with the x-ray source 43. Based on the received pulse data, the flat panel control module may generate the flat panel detector data (and/or a corresponding signal) for the IPM 47.

Based on the motion profile data, the processor 39 may generate rotor move data (and/or a corresponding signal) for the GCM 85. The rotor move data may indicate a selected movement profile for the rotor 46 to move within the gantry 42 to enable the acquisition of the image data. The GCM 85 may receive as an input the rotor move data. Based on the rotor move data, the rotor 46 may be moved within the gantry 42 to a desired location in order to acquire the image data.

Figure 3:
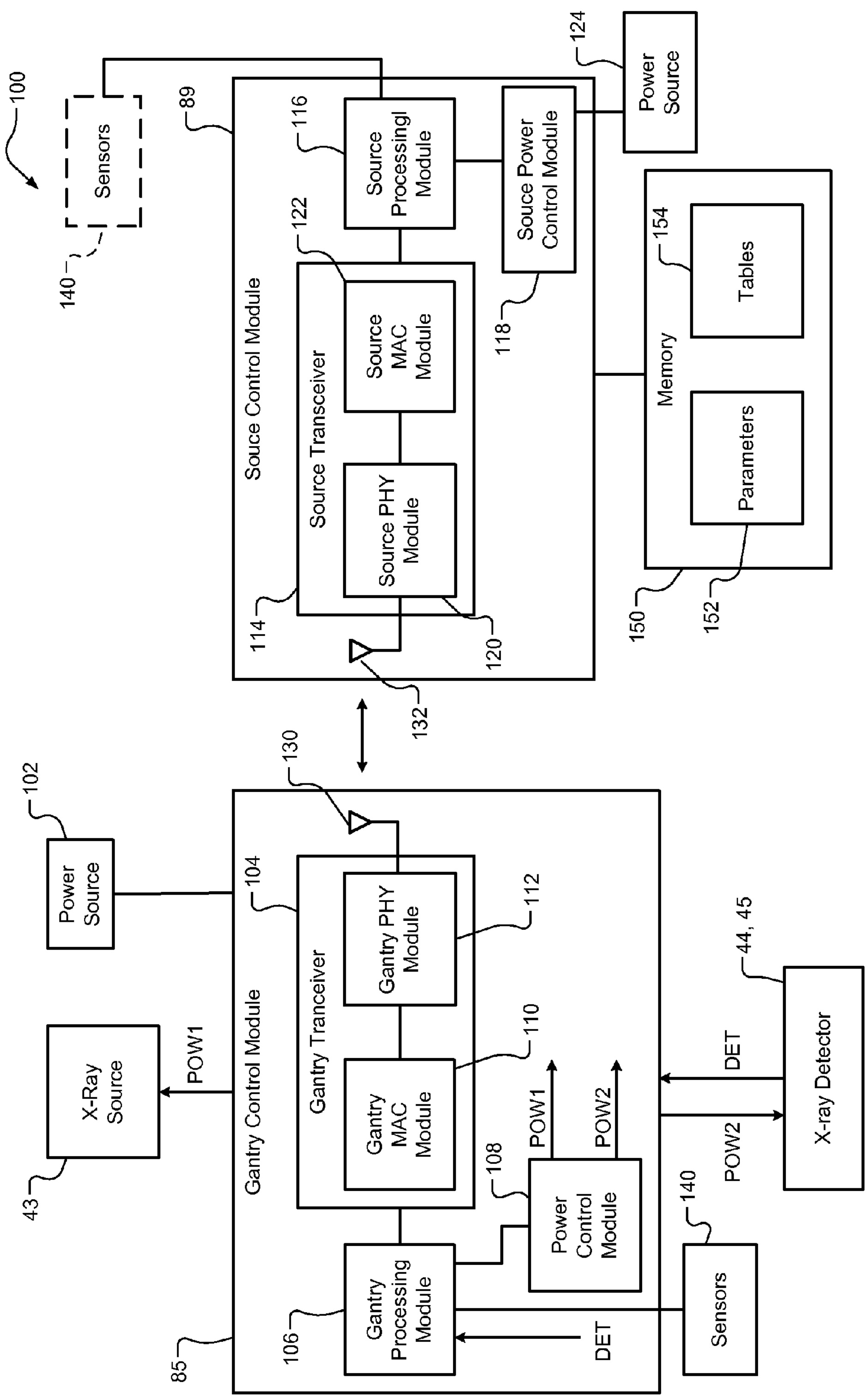
FIG. 3 is functional block diagram of a portion of an imaging system of FIG. 1 or 2.

FIG. 3. shows a portion 100 of the imaging system 33 of FIG. 2. The portion 100 may include the x-ray source 43, the GCM 85, the SCM 89, the x-ray detectors 44, 45 and a power source 102. The GCM 85 may include a gantry transceiver 104, a gantry processing module 106 and a gantry power control module 108. The gantry transceiver 104 may include a gantry medium access control (MAC) module 110 and a gantry physical layer (PHY) module 112. The gantry transceiver 104, the gantry processing module 106 and the power control module 108 may receive power from the power source 102.

The SCM 89 includes a source transceiver 114, a source processing module 116, and a source power control module 118. The source transceiver 114 includes a source PHY module 120 and a source MAC module 122. The source transceiver 114 and the source processing module 116 may receive power from the source power control module 118, which receives power from a second power source 124.

The gantry processing module 106 may wirelessly communicate with the source processing module 116 via the transceivers 104, 114 and respective antennas 130, 132. The gantry processing module 106 may receive sensor signals and/or information from sensors 140 directly or from the source control module 89. The gantry processing module 106, based on signals from the source processing module 116, may control (i) power supplied to and/or position and speed of the rotor 46, and (ii) power supplied to the x-ray source 43. The source processing module 116 may generate a mode signal, which is provided to the gantry power control module 108. The gantry power control module 108 may supply power to actuators, motors, the x-ray source 43, and/or the detectors 44, 45 based on the operating mode indicated by the mode signal. The power supplied to the x-ray source 43 and the detectors 44, 45 are shown as POW1 and POW2.

The source MAC module 122 generates control signals based on data and/or information received from the source processing module 116. The source PHY module 120 wirelessly transmits the control signals to the gantry PHY module 112. The source MAC module 122 may generate information signals based on data and/or information received from the source processing module 116. The information signals are transmitted wirelessly via the source PHY module 120 to the gantry PHY module 112. The gantry processing module 106 may control operation of the devices (e.g., x-ray source 43, x-ray detectors 44, 45, power control module 108, etc.) based on the information signals and/or signals from the sensors 140.

The gantry power control module 108 may receive power from a generator (e.g., power source 102) or other power source. The power sources 102, 124 may be the same or different power sources. The power may be based on sensor signals from the sensors 140, which may be connected to the gantry control module 85 and/or the source control module 89.

The source control module 89 and/or the source processing module 116 may be connected to and/or access a memory 150. The memory 150 may store various parameters (or settings) 152 and tables 154. The parameters 152 may include any of the parameters herein described including procedure parameters, patient parameters, surgeon parameters, recommended parameters, etc. The tables 154 may relate procedure, patient and surgeon parameters to recommended parameters. The tables 154 are not static, but rather may be continuously modified and added to prior to, during and/or subsequent to procedures performed.

Figure 4:
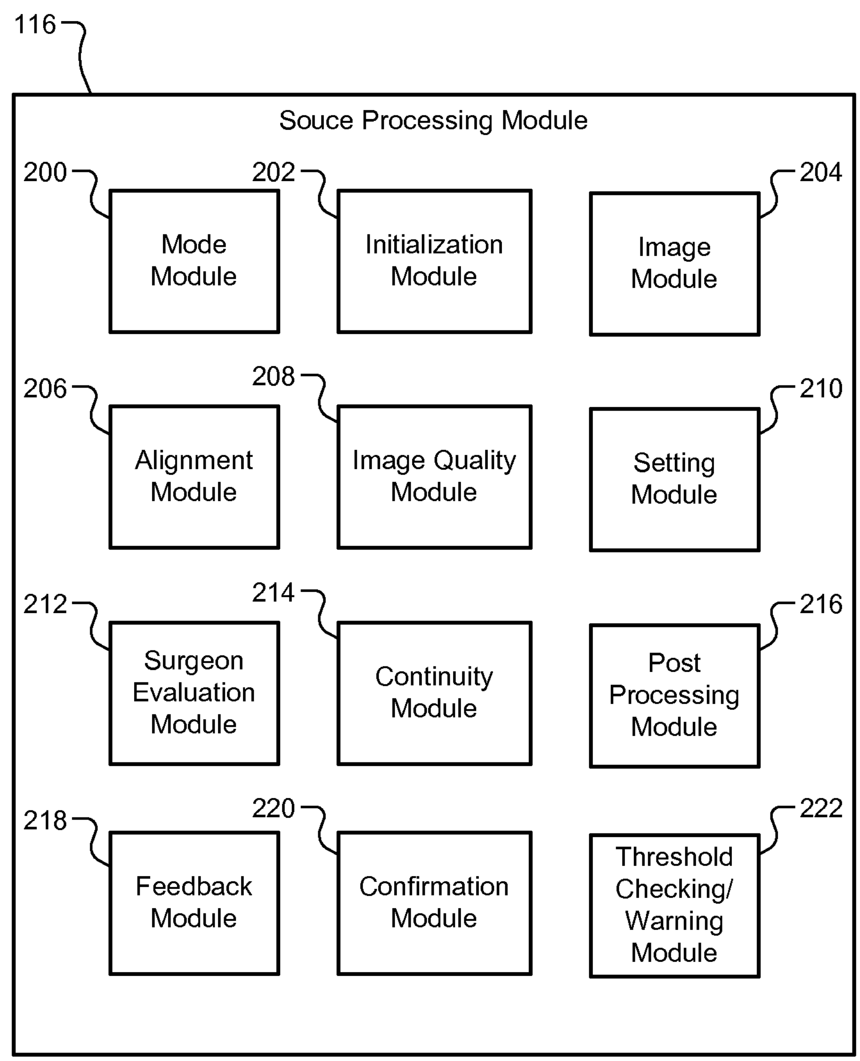
FIG. 4 is a functional block diagram of a navigation processing module in accordance with an embodiment of the present disclosure.

FIG. 4 shows an example of the source processing module (SPM) 116, which may include a mode module 200, an initialization module 202, an image module 204, an alignment module 206, an image quality module 208, a setting module 210, a surgeon evaluation module 212, a continuity module 214, a post processing module 216, a feedback module 218, a confirmation module 220, and a threshold checking and waring module 222. These modules are described below with respect to FIGS. 5A-5B.

Figure 5A:
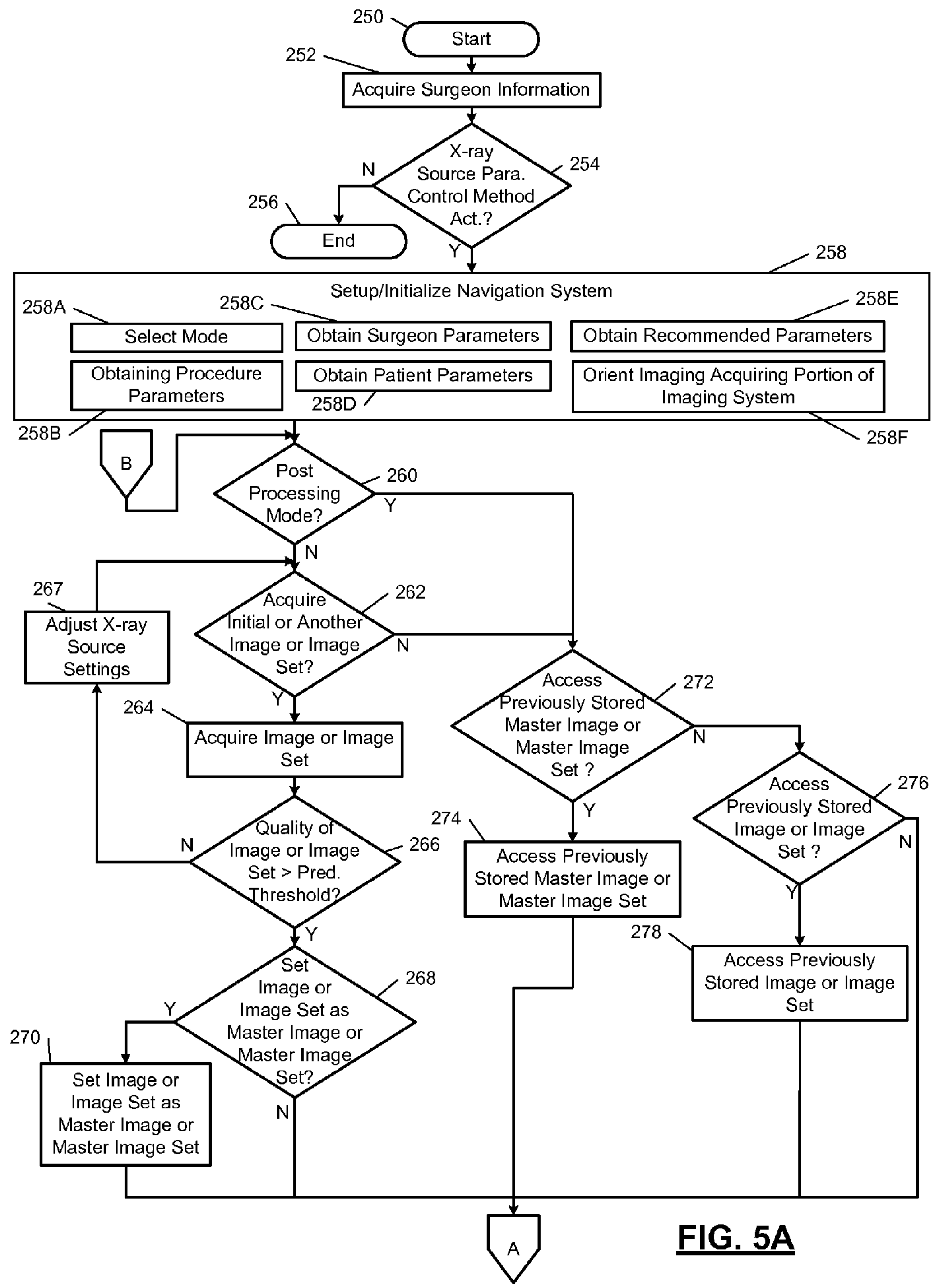
FIGS. 5A-5B illustrate a method of operating a procedural operating system in accordance with an embodiment of the present disclosure.
Figure 5B:
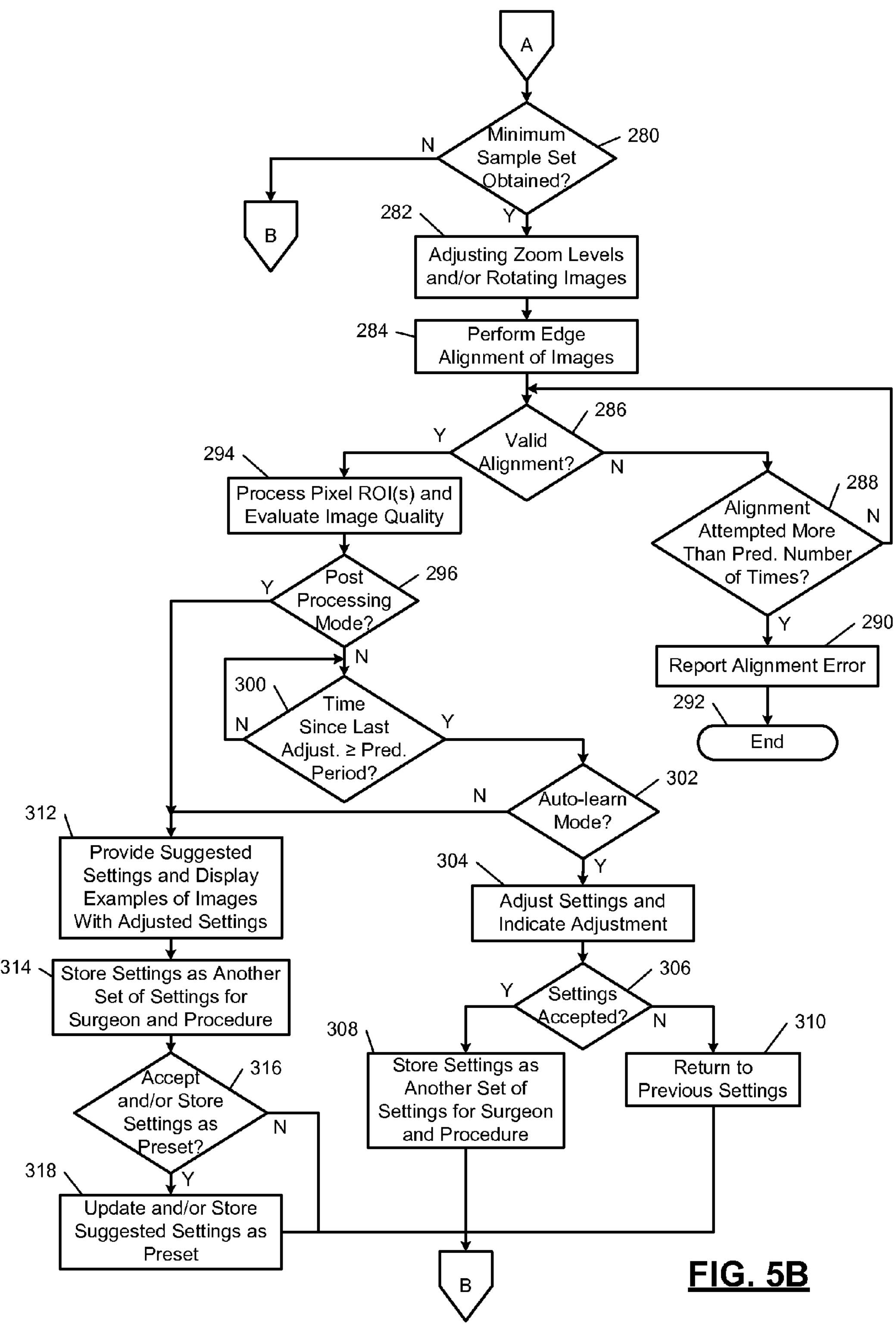

For further defined structure of the modules of FIGS. 1-4 see below provided method of FIGS. 5A-5B4 and below provided definition for the term "module". The systems FIGS. 1-2 and/or portions thereof may be operated using numerous methods, an example method is illustrated in FIGS. 5A-5B. In FIGS. 5A-5B, a method of operating a procedural operating system or a portion thereof is shown. Although the following tasks are primarily described with respect to the implementations of FIGS. 1-4, the tasks may be easily modified to apply to other implementations of the present disclosure. The tasks may be iteratively performed.

The method may begin at 250. At 252, surgeon information is acquired via an input device (e.g., the input device 38 and/or scanner). The surgeon information may include, for example, a surgeon ID or other identification information. The surgeon information may be uploaded automatically when an ID badge of the surgeon is swiped and/or scanned via the input device. The surgeon information may include a selected procedure and/or surgeon parameters including x-ray source parameters for procedures conducted by the surgeon. The selected procedure may be indicated by the surgeon via the input device.

At 254, the SPM 116 may receive an input from the surgeon which activates an x-ray source parameter control method. The SPM 116 may activate the method based on the input. Task 258 may be performed if the method is activated. The x-ray source parameter control method may include the following tasks 258-318. This method may be activated when the surgeon, for example, enters the surgeon information and/or swipes or scans an ID badge at the input device. The SPM 116 may verify the surgeon information prior to permitting the method to be activated. If the method is not activated and/or the surgeon information is not approved, the method may end at 256.

At 258, the SPM 116 performs a setup and/or initialization process to setup and/or initialize the imaging system 33. This may include selecting an operating mode (258A), obtaining procedure parameters (258B) if not already obtained, obtaining surgeon parameters (258C) if not already obtained, obtaining patient parameters (258D) for a selected procedure if not already obtained, obtaining recommended parameters (258E) for the procedure being performed, and orienting imaging acquiring portion of the imaging system (258F). Initial x-rays source settings may be set as described below based on one or more of the parameters obtained during task 258. For example, x-ray source voltages, current levels and dosage periods may be selected based on patient parameters such as body size, region-of-interest, shapes of bones and/or organs, etc. As another example, the x-ray source parameters may be set based on other parameters, such as pixel intensities of previously stored images for the selected procedure, etc. The x-ray source settings may be set to last or preset settings for the surgeon, site, imaging system, patient, and/or procedure being performed.

At 258A, mode module 200 selects an operating mode. The mode module 200 selects an operating mode of the SPM 116 and/or other modules of the imaging system 33. The modes may include an auto-learn mode, a manual mode, a post processing mode, a patient specific mode and/or a non-patient specific mode. The mode module 200 may select one or more of the modes to operate in during the same period of time. For example, the mode module 200 may select operation in one of the auto-learn mode, manual mode and post processing mode and may also select operation in one of the patient specific and non-patient specific modes.

During the auto-learn mode parameters are monitored, tracked and used to adjust x-ray source settings to recommended levels. During the auto-learn mode, settings may be automatically adjusted to recommended levels and a confirmation of the recommended levels may be requested from a surgeon (or user). During the manual mode, parameters are monitored, tracked and used to recommend x-ray source settings. During the manual mode, the recommended levels are indicated, but the x-ray source levels are not automatically adjusted. The x-ray source settings are not adjusted without surgeon acceptance and/or setting of recommended levels. The auto-learn mode and the manual mode may be performed prior to and/or during a procedure.

The post processing mode may be performed subsequent to a procedure and/or while a procedure is not being performed. The post processing mode allows a surgeon to view and evaluate images taken during a procedure and to post process the images based on different x-ray source settings than that used during the procedure. This allows a surgeon to determine improved x-ray source settings for subsequent procedures. System recommended settings may be provided to the surgeon during the post processing mode as described below.

At 258B, 258C, 258D, 258E, parameters may be loaded from a memory (e.g., the memory 150), a central provider device 14 and/or other storage device and/or centrally accessible device to the SPM 116. The parameters may all be associated with the selected procedure and/or a similar procedure. The parameters may include default parameters if, for example, parameters are not available or are partially available for the selected procedure. The default parameters may be surgeon specific or independent of the surgeon performing the selected procedure. X-ray source parameters may be selected by the setting module 210 and/or by the surgeon. The surgeon may approve the selected settings. For example, the setting module 210 may (i) select recommended, preset, default, and/or surgeon preferred settings, and then (ii) generate a request for the surgeon to confirm the settings. The surgeon may then confirm the settings and/or modify the settings prior to proceeding to task 260. At 258F, the imaging acquiring portion (e.g., the detectors 44, 45) may be oriented to target and/or predetermined initial positions prior to being the selected procedure.

At 260, the post processing module 216 and/or SPM 116 may determine whether the post processing mode has been selected. If the SPM 116 is not operating in the post processing mode, task 262 is performed, otherwise task 272 is performed.

At 262, the image module 204 may determine whether to acquire an image or set of images. The image or set of images may be (i) an initial (or baseline) image or set of images, (ii) an additional image or set of images, (iii) an image or set of images to be used as a master image or master set of images. A single image of a region-of-interest may be acquired or a set of images (e.g., slices of images of a region or body part (e.g., one or more bones and/or organs) of interest may be acquired. Each image or set of images acquired during an iteration of task 264 may be referred to as a sample set. The determination of whether an image or image set is to be acquired may be based on whether a master image/image set is available and/or a predetermined minimum sample set is satisfied. The predetermined minimum sample set may require one or more images of a region-of-interest and/or one or more images of each slice of a region and/or one or more body parts. If an image or set of images are to be acquired, task 264 is performed, otherwise task 272 is performed.

At 264, the image module 204 may acquire an initial image or set of images or another image or set of images, as described for task 262. The image module 204 may control the x-ray source 43 and the detectors 44, 45 to acquire the image(s). The x-ray source 43 may be operated using x-ray source parameters loaded and/or selected in prior tasks.

At 266, the image module 204 and/or the quality module 208 may determine quality of the image(s) acquired at 264 are greater than a predetermined threshold. This may include determining pixel intensities and/or other pixel parameters (contrast ratios, brightness levels, etc.) and comparing to predetermined values to determine the quality of the image(s). The image quality values may be based on surgeon inputs indicating a surgeon ranking of the quality levels of the images. If there is more than one image, an average quality value may be determined for the images and compared to the predetermined threshold. If the quality of the acquired images is less than the predetermined threshold, task 267 may be performed, otherwise task 268 may be performed. If task 267 is performed, the acquired images may be discarded and/or stored for future reference.

At 267, the x-ray source settings may be adjusted. The surgeon may manually adjust the settings or the settings may be automatically adjusted and the surgeon may be prompted to confirm the settings based on the operating mode. If operating in the manual mode, the adjusted settings may be recommended based on historical data and the surgeon may then accept the setting, maintain the current settings, or input different settings. If operating in the auto-learning mode, recommended adjustments (updated settings) may be provided and set and the surgeon may be prompted to confirm the updated settings. If the surgeon does not accept the updated settings, the previous settings are maintained unless the surgeon enters different settings and/or adjustment values. Similar tasks are performed at 302-318. Task 262 is performed subsequent to task 267.

At 268, the image module 204 may determine whether to set the acquired image or image set as the master image or master image set. This may occur, for example, if a previous master image or master image set is not already stored and/or acquired. This may also or alternatively occur if the surgeon indicates via the input device for the most recently acquired image or image set be the master (or preset) image or master (or preset) image set. Task 270 is performed if the last acquired image or image set is to be the master image or master image set, otherwise task 280 is performed. At 270, the last acquired image or image set is tagged to be identified as the master. Subsequently acquired images may be compared to the master. Task 280 may be performed subsequent to task 270.

At 272, the image module 204 may determine whether to access a previously stored master image or master image set. Task 272 may be performed while operating in the auto-learn mode, the manual mode or the post processing mode. This may be based on an input received from the surgeon and/or a setting stored and associated with the surgeon indicating access of the master image or master image set. The master image/image set may be stored in the above-mentioned memory. The master image/image set may be a last acquired image/image set. Task 274 is performed if a master image/image set is accessed, otherwise task 276 is performed. At 274, the image module 204 accesses the previously stored master image/image set. Task 280 may be performed subsequent to task 274.

At 276, the image module 204 may determine whether to access a previously stored image or image set (i.e. non-master image/image set). This may be based on an input received from the surgeon and/or a setting stored and associated with the surgeon indicating access of the image or image set. The image/image set may be stored in the above-mentioned memory. The image/image set may be a last acquired image/image set or other image/image set. Task 278 is performed if an image/image set is accessed, otherwise task 280 is performed. At 278, the image module 204 accesses the previously stored image/image set.

At 280, the image module 204 may determine whether the predetermined minimum sample set threshold has been met. If this threshold has been met, task 282 is performed, otherwise task 260 may be performed.

At 282, the alignment module 206 may adjust zoom levels and/or rotate one or more of the acquired and/or accessed image(s) to corresponding ones of the master image(s). At 284, the alignment module 206 performs edge alignment to align the master, acquired, and/or accessed images and/or portions thereof relative to each other. This may include comparing pixel parameters (e.g., brightness, intensity levels, color, contrast ratios, sharpness values, etc.) for the images to find edges of bones, tissue, organs, body parts, regions of interest, etc. Differences in adjacent pixels may be determined to located edges. A predetermined number of pixels of each of the images in respective quadrants of the images may be compared. As an example, a predetermined number of brightest pixels and/or pixels providing a predetermined pattern may be compared to align the images and/or portions thereof. Horizontal rows and/or vertical rows of pixels may be compared. Full or partial portions of the images may be scanned to provide a "best-fit" alignment. As another example, each of the pixels has a unique set of values (e.g., red, green and blue values), which may be compared to provide a best-fit alignment. Differences between the red, green and blue values adjacent pixels of each image may be compared to differences between red, green and blue values of adjacent pixels of the other images to provide the best-fit alignment. Edge alignment can be performed to minimize and/or eliminate offsets between the images and/or portions thereof. The images may be scaled prior to and/or during alignment based on x-ray source settings used for each of the images.

At 286, the alignment module 286 may determine whether a valid alignment of the images or portions thereof has been established. If differences between corresponding pixels of different images are on average within a predetermined range or if transitions (differences between adjacent pixels) of each image are within predetermined ranges of each other, then a valid alignment may have been performed. Task 288 may be performed if an invalid alignment has been performed, otherwise task 294 may be performed.

At 288, the alignment module 288 may determine if an alignment has been attempted (task 284 has been performed) more than a predetermined number of times for the current images. If an alignment has been attempted more than the predetermined number of times, then task 290 is performed, otherwise the alignment module 288 returns to task 286. At 290, an alignment error may be reported to the surgeon via, for example, the display device 35. If task 290 is performed, the SPM 116 may return to task 260 to acquire and/or access additional images. Subsequent to task 290, the method may end at 292.

At 294, the quality module 208 may process a result of the alignment including the aligned images. This may include processing pixel regions-of-interest and evaluating separate and/or combined image quality values of (i) the images separately prior to alignment, and/or (ii) a combined result of the aligned images subsequent to alignment. In one embodiment, pixel regions-of-interest of the latest sample set of images after alignment are alone processed to provide image quality values.

During task 294, a second set of image quality values (or one or more sets of image quality values) may be determined. The processing of results of the alignment may be based on pixel parameters (e.g., pixel intensity values, continuity values, or other herein disclosed pixel parameters) and/or patient parameters, which may be compared with predetermined values and/or weighted and then compared to predetermined values. The weighted values may be based on pixel parameters; average pixel intensity levels of the images; patient parameters; age of the images; whether the images are of the current patient; whether the images are for the current procedure or a similar procedure; quality levels as indicated by the surgeon; and/or other stored quality values; etc. The determined second set of quality values may be determined based on a number and/or percentage of pixels within a region-of-interest that have pixel parameters within predetermined respective ranges.

At 296, the SPM 116 and/or post processing module 216 may proceed to task 300 if not operating in the post processing mode, otherwise may proceed to task 312. At 300, the setting module 210 may determine whether an amount of time since a last adjustment of the x-ray source settings is greater than or equal to a predetermined period. If the amount of time since the last adjustment is greater than or equal to the predetermined period, then task 302 may be performed.

At 302, the SPM 116 continues to task 304 if operating in the auto-learn mode, otherwise the SPM 116 performs task 312. At 304, the setting module 210, continuity module 214, and/or SPM 116 adjusts the current x-ray source settings to updated values. This may include determining adjustments to current values and/or updated values. This may include providing calculated, looked-up and/or recommended adjustments and/or updated values. The adjustments and/or updated values may be determined based on the tables 154, which may relate procedure parameters, patient parameters, surgeon parameters, x-rays source parameters, and image quality values for the patient 32, the imaging system 33, and/or other patients and imaging systems to provide recommended x-rays source settings for maximum image quality and minimum x-ray dosage. During the patient specific mode only values pertaining to the patient 32 may be used. During the non-patient specific mode, values of other patients may be used. Maximum image quality and minimum x-ray dosage values may have been previously verified. The updated settings may provide reduced x-ray dosage values as compared to the previously used settings. This may be based on the second set of quality values determined at 294 and/or any of the parameters obtained during task 258. The tables may be multi-dimensional tables having any number of different parameters.

If there is lack of continuity between current images (or currently acquired images) and previously stored images, then default x-ray source settings or best-fit settings may be selected. For example, this may occur if there are a lack of records with images for the patient (non-standard patient or non-typical patient) and/or condition of the patient for which the procedure is being performed. For example, there may be a lack of images for rare conditions, such as scoliosis or other rare conditions.

At 306 and while operating in the auto-learn mode, the confirmation module 220 may request the surgeon to confirm the updated settings. If the updated settings are confirmed, task 308 is performed, otherwise task 310 is performed. At 308, the adjusted settings are maintained for subsequent imaging and/or processing and may be stored in the memory and/or provided to the central provider device 14 for future use by the imaging system 33 and/or other imaging systems. At 310, the confirmation module 220 returns to the x-ray source settings used prior to the update and does not maintain the updated settings. Subsequent to tasks 308, 310, task 260 may be performed.

At 312, the setting module 210 and/or the post processing module 216 while operating in the post processing mode or manual mode provides the settings determined at 304. The settings may be indicated via the display to the surgeon. The surgeon may then continue the current settings and/or accept the recommended settings. If the recommended settings are accepted, as determined at 316, the setting module updates the settings. If the settings are not accepted task 360 may be performed. Task 312 may also include displaying modified images based on the updated settings to provide examples of how the images would look if the updated settings were used. This may include post processing the images using filters and/or other image enhancement techniques. This may include adjusting pixel intensities of the images. The surgeon may be prompted of the difference in x-ray dosage for the updated x-ray source settings relative to the x-ray dosage exhibited for x-ray source settings used to provide the previously acquired and/or accessed images.

At 314, the updated settings may be stored as another set of settings for the surgeon and/or procedure, as performed at 308. At 316, if the updated settings are accepted and/or to be stored as preset (or master) settings, task 318 is performed, otherwise task 260 is performed. The surgeon may be prompted as to whether the updated settings are to be stored as preset or master settings for future iterations of this method.

The above-described tasks are meant to be illustrative examples; the tasks may be performed sequentially, synchronously, simultaneously, continuously, during overlapping time periods or in a different order depending upon the application. Also, any of the tasks may not be performed or skipped depending on the implementation and/or sequence of events.

The SPM 116 and/or the surgeon evaluation module 212 of the imaging system 33 may monitor trends of surgeons. This may include monitoring x-rays source parameter trends of a particular surgeon relative to x-ray source trends of other surgeons for similar patient parameters and procedure parameters. These trends may also be compared to recommended x-ray source settings. The feedback module 218 may provide feedback to a surgeon and/or other user via the display device 35 indicating whether the surgeon is following trends of other surgeons or is using x-ray source settings that result in poorer image quality and/or higher x-ray dosages. The feedback may be provided to and/or similarly determined by the central provider device 14. The feedback may also indicate whether the trends of a surgeon are away from recommended settings and/or typical differences between the surgeon settings and the recommended settings. The surgeon evaluation module 212 may also predict a trend of a surgeon for a particular patient and/or procedure. For example, if the surgeon is gradually increase or decreasing x-ray source settings over time or is consistently using certain x-ray source settings, this information may be indicated via the display device.

The post processing mode allows a surgeon to evaluate images acquired during a surgery using the above-described method and then use updated settings determined by the method in subsequent procedures for improved image quality and/or reduced x-ray dosage.

The threshold checking/warning module 222 may determine if the x-ray source settings selected by a surgeon are outside predetermined ranges of (i) settings typically used by other surgeons for a similar patient and a similar procedure, and/or (ii) recommended (central prover and/or industry recommended) settings. If outside the stated predetermined ranges and/or any of the x-ray source settings are greater than or equal to predetermined maximum values, then the threshold checking/warning module 222 may prompt the surgeon to change the selected settings. Typical surgeon settings and/or recommended settings may be indicated to the surgeon and the surgeon may be prompted whether the typical surgeon settings and/or recommended settings are acceptable. Sample images may be provided for the typical surgeon settings and/or recommended settings, as described above. The threshold checking/warning module 222 may prompt a user and/or prevent imaging if one or more of the x-ray source settings are outside a predetermined range, which would result in x-ray dosage greater than a predetermined level.

The above-disclosed methods allow post analysis of images to provide radiation trends using image detection algorithms and regions-of-interest. Target and/or recommended x-ray source settings may then be provided based on estimated and/or determined patient parameters (e.g., body habitus) to then provide recommended settings back to the user. This includes types of images that an imaging system at a particular site typically provides for the recommended settings. Information pertaining to how an imaging system is being used at a particular site may be provided back to a central provider device and/or indicated to the user and/or a technician.

In the above-described method, image sample sets may be acquired at predetermined frequencies such that post processing of the images may be performed. Parameters associated with each of the image sets may be logged for future evaluation. Each image set may be for a particular patient, surgeon, one or more procedures, one or more regions-of-interest, etc.

The wireless communications described in the present disclosure can be conducted in full or partial compliance with IEEE standard 802.11-2012, IEEE standard 802.16-2009, IEEE standard 802.20-2008, and/or Bluetooth Core Specification v4.0. In various implementations, Bluetooth Core Specification v4.0 may be modified by one or more of Bluetooth Core Specification Addendums 2, 3, or 4. In various implementations, IEEE 802.11-2012 may be supplemented by draft IEEE standard 802.11ac, draft IEEE standard 802.11ad, and/or draft IEEE standard 802.11ah.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including “connected,” “engaged,” “coupled,” “adjacent,” “next to,” “on top of,” “above,” “below,” and “disposed.” Unless explicitly described as being “direct,” when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean “at least one of A, at least one of B, and at least one of C.”

In this application, including the definitions below, the term “module” or the term “controller” may be replaced with the term “circuit.” The term “module” may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. A system comprising:
- an initialization module configured to obtain patient parameters for a first patient, procedure parameters, and surgeon parameters, wherein the initialization module is configured to select a first plurality of settings for an x-ray source based on the patient parameters, the procedure parameters, and the surgeon parameters;
- an image module configured to obtain (i) a first sample set of one or more images of a region-of-interest of the first patient, and (ii) a master sample set of one or more images, wherein the first sample set of one or more images were acquired as a result of the x-ray source operating according to the first plurality of settings;
- an alignment module configured to align the first sample set of one or more images to the master sample set of one or more images;
- a processing module configured to process pixel data corresponding to a result of the alignment based on a pixel parameter or one of the patient parameters; and
- a setting module configured to adjust the first plurality of settings to provide updated settings, wherein x-ray dosage associated with the updated settings is less than x-ray dosage associated with the first plurality of settings.

2. The system of claim 1, wherein:
- the image module is configured to acquire the master sample set of one or more images based on a second plurality of settings of the x-ray source; and
- the second plurality of settings is different than the first plurality of settings.

3. The system of claim 1, wherein the master sample set of one or more images is obtained prior to the first sample set of one or more images and prior to or during a same procedure as the first sample set of one or more images.

4. The system of claim 1, wherein the first sample set of one or more images are acquired while operating in an auto-learn mode or a manual mode.

5. The system of claim 1, wherein the first sample set of one or more images are accessed from a memory during a post processing mode.

6. The system of claim 1, further comprising a quality module configured to (i) determine quality of the first sample set of one or more images, and (ii) instruct the image module to acquire a second set of one or more images based on the quality of the first sample set of one or more images.

7. The system of claim 1, wherein the image module is configured to (i) determine if a minimum sample set is available prior to the processing module processing the pixel data, and (ii) if the minimum sample set is not available, acquire or access a second sample set of one or more images.

8. The system of claim 7, wherein the second sample set of one or more images is of the region-of-interest of the first patient or is of a region-of-interest of a second patient.

9. The system of claim 1, wherein the patient parameters include parameters corresponding to the first patient and parameters corresponding to a second patient.

10. The system of claim 1, wherein the surgeon parameters include surgeon parameters for a plurality of surgeons.

11. The system of claim 1, wherein the setting module is configured to determine updated settings for the x-rays source based on: a size of the first patient; the region-of-interest of the patient; pixel intensity levels of the first sample set of one or more images and master sample set of one or more images; and continuity of the first sample set of one or more images.

12. The system of claim 11, wherein the continuity of the first sample set of one or more images refers to similarity between the first sample set of one or more images and other stored sample sets of one or more images.

13. The system of claim 11, wherein setting module is configured to, during an auto-learn mode, (i) adjust the first plurality of settings to the updated settings, and (ii) prompt a surgeon for confirmation of the updated settings.

14. The system of claim 11, wherein the setting module is configured to, during a manual mode, (i) prompt a surgeon of the updated settings without adjusting the first plurality of settings, and (ii) adjust the first plurality of settings to the updated settings if an input is received indicating confirmation of the updated settings.

15. The system of claim 11, wherein:
- the first plurality of settings are used to acquire the first sample set of one or more images during a first procedure; and
- the setting module is configured to store the first plurality of settings as a preset or as an updated master sample set of one or more images for a second procedure.

16. The system of claim 1, wherein the alignment module is configured to (i) rotate and adjust zoom levels of the first sample set of one or more images for alignment with the master sample set of one or more images, and (ii) verify alignment of the first set of one or more images with the master sample set of one or more images.

17. The system of claim 1, further comprising a feedback module configured to provide feedback indicating whether one or more the first plurality of settings for a procedure are outside (i) one or more respective ranges of typical settings used for the procedure, or (ii) one or more respective ranges of recommended settings for the procedure.

18. The system of claim 1, further comprising a threshold module configured to generate a warning signal to indicate that one or more of the first plurality of settings is outside one or more ranges indicating x-ray dosage resulting from use of the first plurality of settings is greater than a predetermined threshold.

19. A method comprising:
- obtaining patient parameters for a first patient, procedure parameters, and surgeon parameters, wherein the initialization module is configured to select a first plurality of settings for an x-ray source based on the patient parameters, the procedure parameters, and the surgeon parameters;
- obtaining (i) a first sample set of one or more images of a region-of-interest of the first patient, and (ii) a master sample set of one or more images, wherein the first sample set of one or more images were acquired as a result of the x-ray source operating according to the first plurality of settings;

aligning the first sample set of one or more images to the master sample set of one or more images;

processing pixel data corresponding to a result of the alignment based on a pixel parameter or one of the patient parameters; and adjusting the first plurality of settings to provide updated settings, wherein x-ray dosage associated with the updated settings is less than x-ray dosage associated with the first plurality of settings.

20. The method of claim 19, further comprising acquiring the master sample set of one or more images based on a second plurality of settings of the x-ray source, wherein the second plurality of settings is different than the first plurality of settings.

21. The method of claim 19, wherein the master sample set of one or more images is obtained prior to the first sample set of one or more images and prior to or during a same procedure as the first sample set of one or more images.

22. The method of claim 19, wherein the first sample set of one or more images are acquired while operating in an auto-learn mode or a manual mode.

23. The method of claim 19, wherein the first sample set of one or more images are accessed from a memory during a post processing mode.

24. The method of claim 19, further comprising:

determining quality of the first sample set of one or more images;

acquiring a second set of one or more images based on the quality of the first sample set of one or more images.

25. The method of claim 19, further comprising:

determining if a minimum sample set is available prior to the processing module processing the pixel data; and if the minimum sample set is not available, acquiring or access a second sample set of one or more images.

26. The method of claim 25, wherein the second sample set of one or more images is of the region-of-interest of the first patient or is of a region-of-interest of a second patient.

27. The method of claim 19, wherein the patient parameters include parameters corresponding to the first patient and parameters corresponding to a second patient.

28. The method of claim 19, wherein the surgeon parameters include surgeon parameters for a plurality of surgeons.

29. The method of claim 19, further comprising determining updated settings for the x-rays source based on: a size of the first patient; the region-of-interest of the patient; pixel intensity levels of the first sample set of one or more images and master sample set of one or more images; and continuity of the first sample set of one or more images.

30. The method of claim 29, wherein the continuity of the first sample set of one or more images refers to similarity between the first sample set of one or more images and other stored sample sets of one or more images.

31. The method of claim 29, further comprising, during an auto-learn mode, (i) adjusting the first plurality of settings to the updated settings, and (ii) prompting a surgeon for confirmation of the updated settings.

32. The method of claim 29, further comprising, during a manual mode, (i) prompting a surgeon of the updated settings without adjusting the first plurality of settings, and (ii) adjusting the first plurality of settings to the updated settings if an input is received indicating confirmation of the updated settings.

33. The method of claim 29, further comprising storing the updated settings as a preset or as an updated master sample set of one or more images for a second procedure, wherein:

the first plurality of settings are used to acquire the first sample set of one or more images during a first procedure; and the second procedure is performed subsequent to the first procedure.

34. The method of claim 19, further comprising:

rotating and adjusting zoom levels of the first sample set of one or more images for alignment with the master sample set of one or more images; and verifying alignment of the first set of one or more images with the master sample set of one or more images.

35. The method of claim 19, further comprising providing feedback indicating whether one or more the first plurality of settings for a procedure are outside (i) one or more respective ranges of typical settings used for the procedure, or (ii) one or more respective ranges of recommended settings for the procedure.

36. The method of claim 19, further comprising generating a warning signal to indicate that one or more of the first plurality of settings is outside one or more ranges indicating x-ray dosage resulting from use of the first plurality of settings is greater than a predetermined threshold.

* * * * *

UNITED STATES PATENT AND TRADEMARK OFFICE

CERTIFICATE OF CORRECTION

PATENT NO. : 9,962,134 B2
APPLICATION NO. : 14/925440
DATED : May 8, 2018
INVENTOR(S) : Richard J. Brody It is certified that error appears in the above-identified patent and that said Letters Patent is hereby corrected as shown below:

In the Claims

Column 22, Line 13, In Claim 11, Line 2, after "on:", insert -- ¶ --;

Column 22, Line 13, In Claim 11, Line 3, after "patient;", insert -- ¶ --;

Column 22, Line 14, In Claim 11, Line 3, after "patient;", insert -- ¶ --;

Column 22, Line 16, In Claim 11, Line 5, after "and", insert -- ¶ --;

Column 23, Line 47, In Claim 29, Line 2, after "on:", insert -- ¶ --;

Column 24, Line 1, In Claim 29, Line 2, after "patient;", insert -- ¶ --;

Column 24, Line 1, In Claim 29, Line 3, after "patient;", insert -- ¶ --;

Column 24, Line 3, In Claim 29, Line 4, after "and", insert -- ¶ --.

Signed and Sealed this
Seventeenth Day of July, 2018

Andrei Iancu
*Director of the United States Patent and Trademark Office*